United States Patent [19]

Congdon

[11] 4,347,849
[45] Sep. 7, 1982

[54] CARDIAC PACER HAVING QUICK-CONNECT LEAD TERMINALS

[75] Inventor: George L. Congdon, Fort Atkinson, Wis.

[73] Assignee: Norland Corporation, Fort Atkinson, Wis.

[21] Appl. No.: 210,276

[22] Filed: Nov. 25, 1980

[51] Int. Cl.³ .............................................. A61N 1/36
[52] U.S. Cl. ................................................. 128/419 P
[58] Field of Search ........ 128/419 P, 419 PG, 419 PS

[56] References Cited

U.S. PATENT DOCUMENTS

| 3,768,487 | 10/1973 | Rose | 128/419 P |
| 4,012,103 | 3/1977 | Lunquist | 128/419 P |
| 4,112,953 | 9/1978 | Shawker | 128/419 P |
| 4,245,642 | 1/1981 | Skubitz et al. | 128/419 P |

FOREIGN PATENT DOCUMENTS 2383532 11/1978 France ............................ 128/419 P

OTHER PUBLICATIONS

Medtronic Publication-TC 68101R, 21 p., Dec. 1968.

Primary Examiner—William E. Kamm
Attorney, Agent, or Firm—Lockwood, Dewey, Alex & Cummings

[57] ABSTRACT

A connector system for use with external cardiac pacers provides an electrical connection to an associated pacer lead assembly. The system includes a pair of terminal blocks each having a bore for receiving a respective connector pin of the lead assembly. A pair of locking plates pivotally mounted in wedge-shaped recesses in the connector blocks each include an aperture through which the connector pins extend. The locking plates are spring-biased into engagement with the connector pins to prevent inadvertent removal of the pins from the bores. An operator actuated release button pivots the locking plates from engagement with the pins to enable the pins to be removed from the pacer.

15 Claims, 7 Drawing Figures

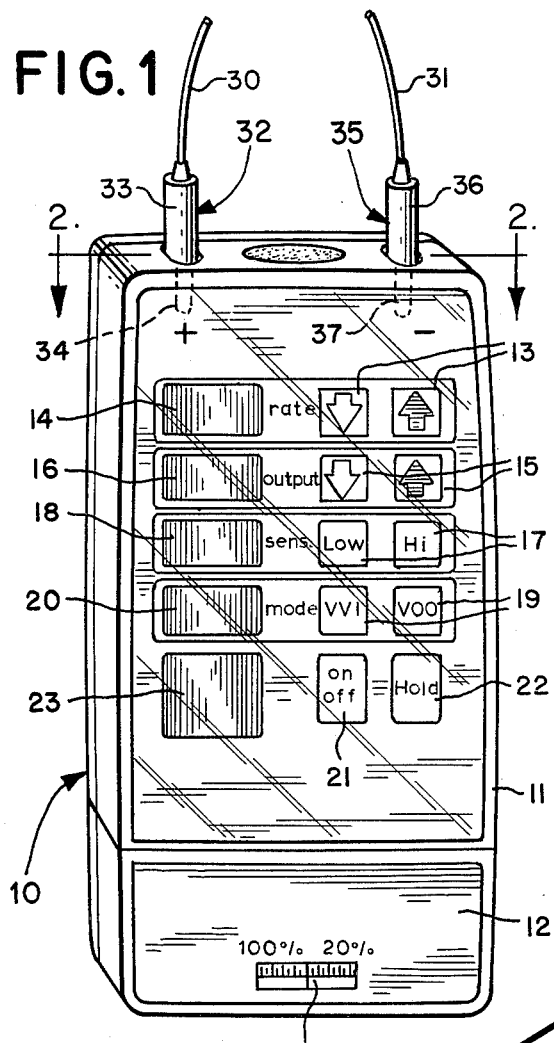

CARDIAC PACER HAVING QUICK-CONNECT LEAD TERMINALS

BACKGROUND OF THE INVENTION

The present invention relates generally to cardiac pacers, and more particularly to an improved connector system for such pacers which provides improved electrical connections to associated pacer leads.

Cardiac pacers, which supply amplitude and rate-controlled electrical pulses to a patient's heart to stimulate muscle contraction, have been developed for portable or temporary external applications, wherein the pacer is externally carried by the patient, and rate, output and sensitivity are adjusted as required by the application. Naturally occurring R-wave signals corresponding to ventricular contraction of the patient's heart are conveyed to such external pacers by means of electrically conductive pacer leads physically attached to the heart. Stimulation pulses generated by the pacer are typically applied to the ventricle of the heart by the same leads to induce muscle contraction.

One difficulty encountered in external pacers is providing an adequate connection between the pacer leads and the pacer. Preferably, such connection must be mechanically and electrically reliable, since separation of the leads from the pacer could have serious consequences in many pacer applications. Furthermore, the connection must not lend itself to inadvertent release, even with continuous handling and movement by the patient. However, when necessary, as when substituting one pacer for another, or when replacing pacer wires, it is necessary that the connection be capable of being quickly released, without undue effort on the part of medical personnel, even under adverse lighting conditions.

Accordingly, it is a general object of the present invention to provide a new and improved external cardiac pacer.

It is a more specific object of the present invention to provide a cardiac pacer having an improved connector system for connection to associated pacer leads.

It is still more specific object of the present invention to provide a new and improved connector system for a cardiac pacer which provides a secure electrical and mechanical connection, and which can be readily released when required by medical personnel.

SUMMARY OF THE INVENTION

The invention is directed, in a cardiac pacer operable with a pacer lead having a connector pin, to a connector which includes connector guide means including a bore dimensioned to receive the pin, and a lock plate including an aperture dimensioned to slidably receive the connector pin. The lock plate is mounted for movement relative to a reference plane perpendicular to the axis of the bore, whereby the aperture is brought into substantial registration with the bore to allow free insertion and removal of the pin when the lock plate is positioned toward parallel alignment with the reference plane, and is brought into substantial misregistration with the bore when the lock plate is moved toward non-parallel alignment with the reference plane to oppose movement of the connector pin through the bore. User actuated means are provided for moving the lock plate from the non-aligned position toward the aligned position to release the connector pin from the connector.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of an external cardiac pacer incorporating a pacer lead connector system constructed in accordance with the invention.

FIG. 2 is an enlarged cross-sectional view of the pacer taken along FIG. 2—2 of FIG. 1.

FIG. 3 is a cross-sectional view of the connector portion of the pacer taken along line 3—3 of FIG. 2 showing the principal components of the connector system.

FIG. 4 is an enlarged exploded perspective view of the pacer lead connector system showing the principal components thereof.

DESCRIPTION OF THE PREFERRED EMBODIMENT

Figure 5:
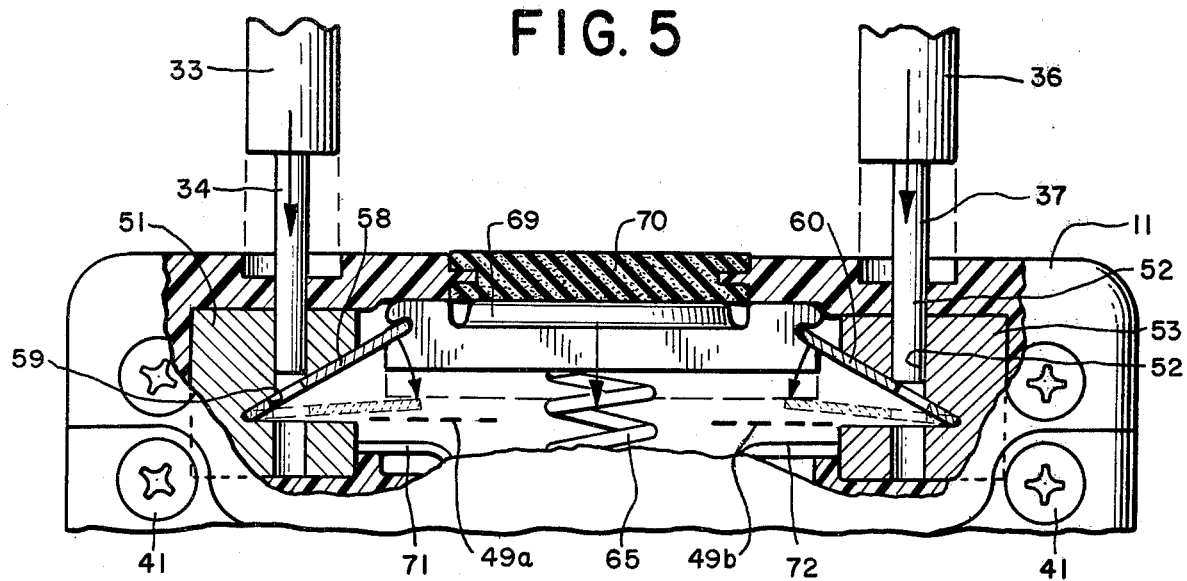
FIG. 5 is an enlarged elevational view of the connector system of the pacer partially broken away to show the principal components thereof during pin insertion.

Referring to the Figures, and particularly to FIG. 1, a portable battery-operated external cardiac pacer 10 constructed in accordance with the invention is seen to include a generally rectangular housing 11 having a detachable battery pack 12 of complementary dimensions. The front panel of housing 11 provides various control and indicator functions for the user. A first set of push button switches 13 is utilized to set output pulse rate, as indicated by a liquid crystal display (LCD) positioned to the left (as viewed in FIG. 1) of switches 13. Output pulse amplitude is controlled by a second set of push button switches 15, the selected pulse amplitude being displayed on a second LCD 16. A pair of push button switches 17 set the sensitivity level of the pacer, as displayed by a third LCD 18. A fourth pair of push button switches 19 set the operating mode of the pacer, as indicated by a fourth LCD 20.

The application of battery power to the pacer is controlled by an ON-OFF push button 21. As a safety measure, a HOLD push button switch 22 must be actuated in order for the other push button switches, except the on function of the on-off switch, to be operable. A fifth LCD 23 displays miscellaneous operating parameters, including the occurrence of sense and pulse functions, and low battery level. Battery life remaining may be indicated by means of an additional indicator 24 located on the front panel of the detachable battery pack.

In accordance with conventional practice, cardiac pacer 10 is connected to a patient's heart by a pair of pacer leads 30 and 31, which may be conventional in design and construction. Pacer leads 32 includes at its pacer end a connector assembly consisting of an electrically non-conductive cylindrical body portion 33, and an electrically-conductive pin portion 34. Similarly, pacer lead 31 includes at its pacer end a connector assembly 35 consisting oan electrically non-conductive body portion 36 and an electrically conductive pin portion 37. As seen in FIG. 1, pacer lead 30 is connected to the position polarity output of the pacer, and pacer lead 31 is connected to the negative polarity output of the pacer. Referring to FIGS. 2 and 3, housing 11 is preferably constructed with a removable back cover 40 secured to a hollow front portion of the housing by a plurality of machine screws 41. When back cover 40 is secured to the front portion of housing 11 as shown in FIGS. 1-3, a compact seamless water-tight housing is formed which protects the circuitry of the pacer in adverse hospital and clinic environments.

When installed, the connector portions of pacer leads 30 and 31 are received within respective apertures 42 and 43 in the top wall (as viewed in FIG. 1) of housing 11. As seen in FIG. 3, apertures 42 and 43 include recessed portions 44 and 45, respectively, of increased diameter at their surface ends to receive a portion of the body portions of connectors 32 and 35. Providing recesses for the body portions of the connector reduces the possibility of inadvertent contact with the electrically-conductive pins 34 and 37 when the pins are inserted. Furthermore, by forming recesses 44 and 45 with one or more flat side surfaces, as shown in FIG. 4, the recesses serve to prevent twisting during the use of lead adaptors, as will be subsequently described.

The front portion of housing 11 is formed with an internal wall 46 which forms in conjunction with the side and top walls of the housing a compartment 47 within which the components of the lead connector are contained. This compartment is preferably water-tight, and appropriate feedthrough bushings or filter terminals 48 may be provided to maintain the liquid-sealed relationship.

Within compartment 47 the pin portion 34 of pacer lead 30 is slidably received within a bore 40 in first pin guide means in the form of a first connector block 51. Similarly, the pin portion 37 of pacer lead 31 is slidably received within a bore 52 in second pin guide means in the form of a second connector block 53. The blocks are positioned at opposite sides of compartment 47 and are held in position by ribs 54 in wall 46. In this position bores 50 and 52 in the connector blocks are axially aligned with apertures 42 and 43, respectively, in the top wall of housing 11.

To lock the electrically-conductive pin portions 34 and 37 in position, connector blocks 51 and 53 are provided with inwardly-facing wedge-shaped recesses 56 and 57 (FIG. 4). Pin locking means in the form of a first lock plate 58 is positioned within wedge 56 with one side thereof adjacent the apex of the wedge, whereby the lock plate is free to pivot about the edge within the recess. The aperture 59 in the lock plate is in substantial alignment with bore 50 of the connector block when the lock plate is pivoted toward a reference plane 49a (FIG. 3) corresponding to the bottom or horizontal wall of the wedge, which is generally perpendicular to the axis of the aligned apertures, to allow free passage of pin 34 through apertures 42, 59, and bore 50. Similarly a second lock plate 60 having an aperture 61 is positioned in the wedge-shaped recess 57 of connector block 53. When lock plate 60 is pivoted toward a reference plane 49b (FIG. 3), in this case the horizontal wall of wedge-shaped recess 57, connector pin 37 may be freely inserted or removed through apertures 43, 61, and bore 52.

To position lock plates 58 and 60, the pacer connector includes, in accordance with the invention, an actuator member 62 adapted to receive in pivotal engagement the free ends of lock plates 58 and 60. As seen in FIG. 3, the actuator member is generally flat and rectangular in construction, and may be molded of plastic or other suitable non-electrically conductive material, and includes at its ends channels 63 and 64 for receiving the ends of the lock plates. The dimensions of actuator member 62 are such that when the member is positioned within compartment 47 with its ends in engagement with lock plates 58 ad 60, the member serves as a bridging element between the lock plates, and the position of the lock plates within their respective recesses in blocks 51 and 53 is dependent on the relative position of the actuator member with respect to the top and bottom walls of the compartment. When the actuator member is near the top or outer wall of compartment 47 the lock plates are pivoted toward the inclined walls of recesses 56 and 57, apertures 59 and 61 are not in good alignment with apertures 42, 43 and bores 50, 52, respectively, and movement of pins 34 and 37 is obstructed. Conversely, when actuator member 62 is positioned closest to inner wall 46, the lock plates are pivoted toward the horizontal walls of recesses 56 and 57, apertures 59 and 61 are in alignment with bores 50 and 52, respectively, and pins 34 and 37 may be freely inserted or removed.

To maintain pins 34 and 37 in a locked condition, the connector includes a helical spring 65 which biases actuator member 62 toward the outside or top wall of compartment 47. To maintain the spring in alignment, the inner wall 46 of housing 11 includes a recess 66 for receiving one end of the spring, and actuator member 62 includes a second recess 67 (FIG. 3) for receiving the other end of the spring.

To enable user-initiated release of pins 34 and 37, the top wall of housing 11 is provided with an aperture 68 through which the user may engage the actuator member 62 to force the actuator member downwardly against the bias of spring 65. To assist the user in this effort, actuator member 62 preferably includes a raised button portion 69 on its top surface which may extend partially into aperture 68. To maintain the liquid-sealed integrity of housing 11, a flexible membrane 70 formed of rubber or other suitable material may be fitted into aperture 68. A tongue-and-groove type engagement may be formed between member 70 and the circumference of aperture 68 for improved sealing and mechanical integrity.

When connector blocks 51 and 53 are installed in compartment 47, electrical connection is established between the blocks and the circuitry of the pacer by conductors 71 and 72, which extend through sleeves 48. Connector blocks 51 and 53, and lock plates 58 and 60, are preferably formed of an electrically conductive metal, and may be plated to improve their electrical contact with pins 34 and 37.

Figure 5A:
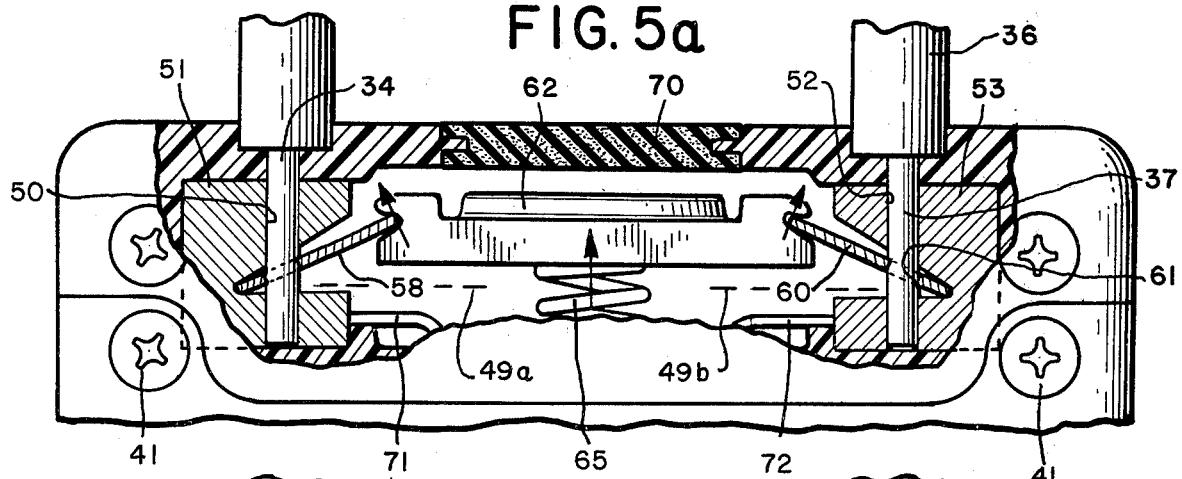
FIG. 5a is an elevational view similar to that of FIG. 5 showing the pin inserted and locked in position.

In use, the locking of pins 34 and 37 is automatic upon insertion of the pins in the pacer. Referring to FIG. 5, upon initial insertion of the pins actuator member 62 is biased against the inside surface of the top wall of housing 11 by spring 65 and lock plates 58 and 60 are pivoted against the upper inclined surface of the recesses of terminal blocks 51 and 53. As pins 34 and 37 are inserted, the ends of the pins engage the lock plates, causing the lock plates to pivot downwardly toward the horizontal surface of the connector block wedges so as to bring apertures 59 and 61 into alignment with bores 50 and 52. As shown in FIG. 5a, this allows the pins to be fully inserted into their respective apertures. It will be appreciated that an attempt at withdrawing the pins will cause lock plates 58 and 60 to attempt to pivot upwardly toward the inclined walls of their respective wedges. This will result in further mis-alignment between aperture 59 and bore 50, and between aperture 61 and bore 52, with the result that the lock plates will tend to lock the pins more firmly in position. The bias exerted by spring 65 on actuator member 62 only serves to enhance the locking capability of the two lock plates.

To unlock the connector pins, it is necessary that the user downwardly displace actuator member 62 against the bias of spring 65 so as to pivot lock plates 58 and 60 toward the bottom or horizontal walls of their respective recesses. This brings apertures 59 and 61 into alignment with bores 50 and 52, respectively, enabling the pins to be freely pulled from the respective apertures. Once the pins have been cleared from the apertures, pressure on diaphragm 70 can be released and spring 65 will return actuator member 62 to the position shown in FIG. 5 in preparation for a subsequent pin insertion.

Figure 6:
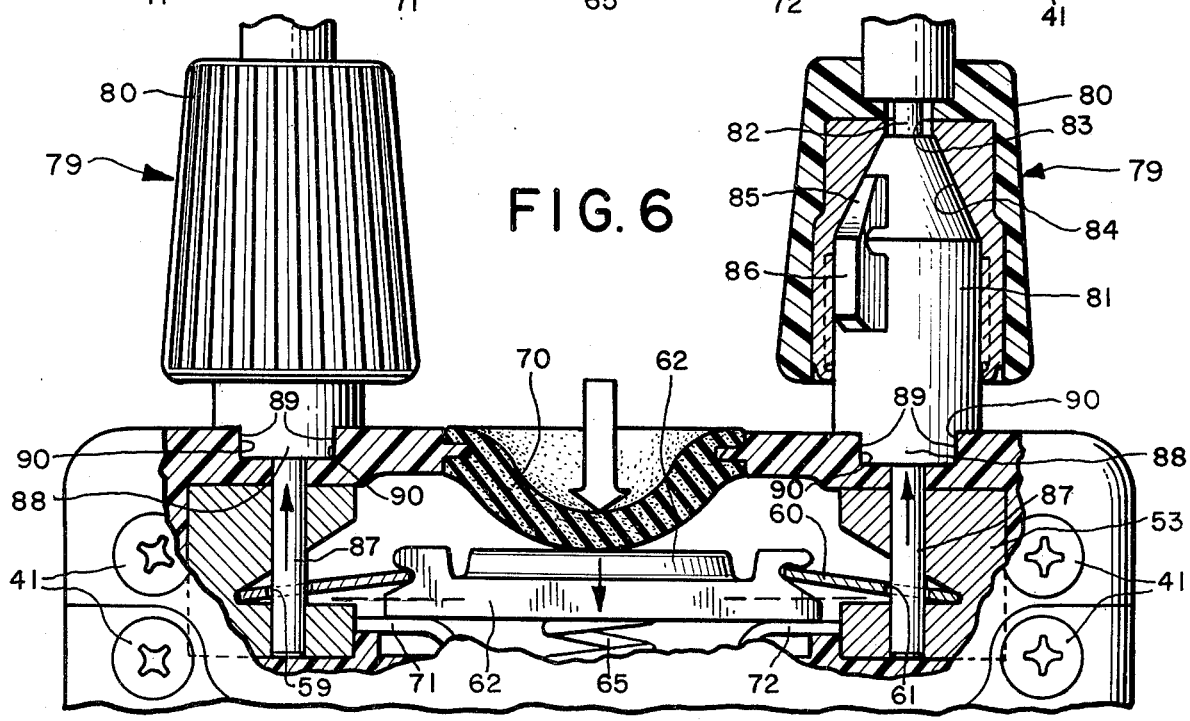
FIG. 6 is an elevational view similar to that of FIG. 5 showing the connector system actuated to release the pins, and showing the use of a pin adaptor.

The pin assemblies shown in FIG. 6 differ from pin assemblies 32 and 35 in that they include a knurled cap 80 having a threaded base portion which may be tightened against a complementarily threaded body portion 81 to secure a pin 82 of smaller diameter than pins 34 and 37. The smaller diameter pin 82 is inserted in an aperture 83 within the cap assembly, and as the cap 80 is tightened a conical engaging surface 84 is brought to bear against a complementarily shaped inclined surface 85 on an electrically conductive pin engaging member 86 to bring the engaging member into tight friction engagement with the inserted pin 82. The engaging member includes an electrically-conductive pin portion 87 identical in diameter to pins 34 and 37 which extends into the apertures of the connector and is locked in position in the manner of pins 34 and 37. In this way, pins of smaller diameter are readily accommodated by the connector.

To prevent the adaptor assembly 79 from turning as the knurled cap 80 is tightened, the bottom portion 88 preferably includes one or more flat surfaces 89 which engage complementarily dimensioned flat surfaces 90 of recesses 44 and 45.

Thus, a connector system for a cardiac pacer has been shown which provides positive locking engagement with inserted pacer leads, without the need for action on the part of the user. Once inserted, the pins are locked and cannot be removed except by the deliberate action of the user in depressing diaphragm 70. The connector system utilizes a minimial number of parts, and is compact in design, so as to lend itself to use in the limited confines of portable pacer housing.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

For example, the reference planes toward which the lock plates are pivoted in releasing the pins may be substantially perpendicular to the axis of the bores as shown, or may be at an angle to the bores with appropriate repositioning of the lock plate apertures for alignment with the bores at the selected angle. Although the reference planes are substantially coplaner in the dual pin embodiment shown, the reference planes need not be so with appropriate repositioning of the actuator member. Furthermore, instead of the lock plates being located in recesses in the connector blocks, they may be located above or below the blocks with appropriate additional mounting means, such as a recess on the housing wall.

I claim:

1. In a cardiac pacer operable with a pacer lead having a connector pin, a connector system comprising:
   connector guide means including a bore dimensioned to receive the pin;
   a lock plate including an aperture dimensioned to slidably receive the connector pin, said lock plate being mounted for movement relative to a reference plane, whereby said aperture is brought into substantial registration with said bore to allow free insertion and removal of said pin when said lock plate is positioned toward parallel alignment with said reference plane, and is brought into substantial misregistration with said bore when said lock plate is moved toward non-parallel alignment with said reference plane to oppose movement of said connector pin through said bore; and
   user actuated means for moving said lock plate from said non-aligned position toward said aligned position to release said connector pin from said connector.

2. A connector system for a cardiac pacer as defined in claim 1 including means for biasing said lock plate toward non-alignment with said reference plane.

3. A connector system for a cardiac pacer as defined in claim 2 wherein said pacer includes a housing having an aperture in substantial alignment with said bore for receiving said connector pin, and wherein said actuator means is actuable from the exterior of said housing.

4. A connector system for a cardiac pacer as defined in claim 1 wherein said reference plane is generally perpendicular to the axis of said bore.

5. A connector system for a cardiac pacer as defined in claim 1 wherein said guide means comprise an electrically conductive connector block, and said lock plate is formed of an electrically conductive material.

6. A connector system for a cardiac pacer as defined in claim 1 wherein said guide means comprise a connector block including a recess, said bore extending through the walls thereof, and wherein said lock plate is pivotally mounted within said recess.

7. A connector system for a cardiac pacer as defined in claim 6 wherein said recess is wedge-shaped, and said lock plate is provided against the apex thereof.

8. A connector system for a cardiac pacer as defined in claim 7 including means for biasing said lock plate away from said reference plane.

9. In a cardiac pacer operable with a pair of pacer leads each having a connector pin, a connector system comprising:
   connector guide means including first and second bores in parallel spaced-apart relationship for receiving respective ones of said connector pins;
   first and second lock plates each including an aperture dimensioned to slidably receive respective ones of said connector pin,
   said lock plates being each mounted for movement relative to a reference plane whereby said apertures are brought into substantial registration with respective ones of said bores to allow free movement of said pins in said bores when said lock plates are positioned toward parallel alignment with said reference plane, and are brought into substantial misregistration with respect one of said bores when said lock plates are moved towards substantial non-parallel alignment with said reference planes to oppose movement of said connector pin through said bores; and user-actuated means for simultaneously moving said lock plates from said non-aligned to said aligned position to release said pins from the connector.

10. A connector system for a cardiac pacer as defined in claim 9 including means for biasing said lock plates toward non-alignment with said reference plane.

11. A connector system for a cardiac pacer as defined in claim 10 wherein said pacer includes a housing having a pair of apertures in substantial alignment with respective ones of said bores for receiving said connector pins, and wherein said actuator means is operatively engaged to said lock plates and is actuable from the exterior of said housing.

12. A connector system for a cardiac pacer as defined in claim 9 wherein said guide means comprise a pair of electrically conductive connector blocks each having one of said bores therein for receiving respective ones of said connector pins.

13. A connector system for a cardiac pacer as defined in claim 12 wherein said connector blocks each include a recess for receiving respective ones of said lock plates, said bores extend through the walls thereof, and said lock plates being pivotally mounted within said recesses.

14. A connector system for a cardiac pacer as defined in claim 13 wherein said recesses are wedge shaped, said lock plates are pivoted against the apexes thereof, and said actuator means are operatively engaged to the free ends of said lock plates and biased to urge said lock plates toward non-alignment with said reference plane.

15. A connector system for a cardiac pacer as defined in claim 9 wherein said reference plane is generally perpendicular to the axis of said bores.

* * * * *